US010052389B2

(12) United States Patent
Kurisawa et al.

(10) Patent No.: US 10,052,389 B2
(45) Date of Patent: Aug. 21, 2018

(54) POLYMERIC SYSTEM FOR RELEASE OF AN ACTIVE AGENT

(71) Applicant: Agency for Science, Technology and Research, Singapore (SG)

(72) Inventors: Motoichi Kurisawa, Singapore (SG); Ki Hyun Bae, Singapore (SG); Fan Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 38 days.

(21) Appl. No.: 14/767,784

(22) PCT Filed: Feb. 13, 2014

(86) PCT No.: PCT/SG2014/000057
§ 371 (c)(1),
(2) Date: Aug. 13, 2015

(87) PCT Pub. No.: WO2014/126537
PCT Pub. Date: Aug. 21, 2014

(65) Prior Publication Data
US 2015/0374838 A1 Dec. 31, 2015

(30) Foreign Application Priority Data
Feb. 13, 2013 (SG) .................................. 201301091

(51) Int. Cl.
| | | |
|---|---|---|
| A61K 47/61 | (2017.01) | |
| A61K 47/69 | (2017.01) | |
| A61K 47/48 | (2006.01) | |
| A61L 27/20 | (2006.01) | |
| A61L 27/22 | (2006.01) | |
| A61L 27/48 | (2006.01) | |
| A61L 27/52 | (2006.01) | |
| A61L 27/54 | (2006.01) | |
| A61L 31/04 | (2006.01) | |
| A61L 31/12 | (2006.01) | |
| A61L 31/14 | (2006.01) | |
| A61L 31/16 | (2006.01) | |
| A61L 15/44 | (2006.01) | |
| A61L 15/60 | (2006.01) | |
| A61K 9/00 | (2006.01) | |
| A61K 47/10 | (2017.01) | |
| A61K 47/36 | (2006.01) | |
| A61K 38/21 | (2006.01) | |
| A61K 38/28 | (2006.01) | |
| A61K 38/38 | (2006.01) | |
| C08B 37/02 | (2006.01) | |
| C08L 5/02 | (2006.01) | |
| A61K 47/60 | (2017.01) | |

(52) U.S. Cl.
CPC ........ *A61K 47/4823* (2013.01); *A61K 9/0019* (2013.01); *A61K 9/0024* (2013.01); *A61K 38/21* (2013.01); *A61K 38/212* (2013.01); *A61K 38/28* (2013.01); *A61K 38/385* (2013.01); *A61K 47/10* (2013.01); *A61K 47/36* (2013.01); *A61K 47/60* (2017.08); *A61K 47/61* (2017.08); *A61K 47/6903* (2017.08); *A61L 15/44* (2013.01); *A61L 15/60* (2013.01); *A61L 27/20* (2013.01); *A61L 27/22* (2013.01); *A61L 27/48* (2013.01); *A61L 27/52* (2013.01); *A61L 27/54* (2013.01); *A61L 31/042* (2013.01); *A61L 31/043* (2013.01); *A61L 31/129* (2013.01); *A61L 31/145* (2013.01); *A61L 31/16* (2013.01); *C08B 37/0021* (2013.01); *C08L 5/02* (2013.01); *A61L 2300/622* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 6,241,787 B1 * | 6/2001 | Nigam ................. | B41M 5/5245 427/355 |
| 6,287,588 B1 | 9/2001 | Shih et al. | |
| 2005/0031588 A1 * | 2/2005 | Sommadossi ...... | A61K 31/7052 424/85.7 |
| 2012/0029089 A1 * | 2/2012 | Chu ..................... | C08F 299/00 514/772.5 |
| 2012/0288564 A1 | 11/2012 | Kurisawa et al. | |

FOREIGN PATENT DOCUMENTS

| | | |
|---|---|---|
| WO | WO-2011/002249 | 1/2011 |
| WO | WO-2011/133113 | 10/2011 |
| WO | WO-2014/126537 | 8/2014 |

OTHER PUBLICATIONS

Harris et al., Effect of Pegylation on Pharmaceuticals, Nature Reviews, Drug Discovery, vol. 2 | Mar. 2003, p. 214-221.*
"International Application No. PCT/SG2014/000057, International Search Report and Written Opinion dated Apr. 22, 2014", (dated Apr. 22, 2014), 9 pgs.
"Singapore Application No. 11201506366S, Written Opinion dated Apr. 28, 2016", (dated Apr. 28, 2016), 14 pgs.
"European Application No. 14751487.1, Extended European Search Report dated Jul. 18, 2016", (dated Jul. 18, 2016), 9 pgs.
Bae, Ki Hyun, et al., "Microstructured dextran hydrogels for burst-free sustained release of PEGylated protein drugs", Biomaterials 63 (2015) 146e157, (Jun. 11, 2015), 146-157.

* cited by examiner

*Primary Examiner* — Jennifer A Berrios
(74) *Attorney, Agent, or Firm* — Schwegman Lundberg & Woessner, P.A.

(57) ABSTRACT

The present disclosure relates to a polymeric system for release of an active agent, comprising a first polymeric phase containing the active agent, the first polymeric phase forming discrete regions of a set size range and being dispersed within a second polymeric phase comprising a cross-linked polymer-phenol conjugate for release of the active agent therein. The present disclosure further provides an injectable hydrogel comprising the disclosed polymeric system, a carrier for delivering a biologically active substance or a drug comprising the injectable hydrogel, and a method for producing the disclosed polymeric system.

16 Claims, 9 Drawing Sheets

POLYMERIC SYSTEM FOR RELEASE OF AN ACTIVE AGENT

PRIORITY CLAIM TO RELATED APPLICATIONS

This application is a U.S. national stage application filed under 35 U.S.C. § 371 from International Application Serial No. PCT/SG2014/000057, which was filed 13 Feb. 2014, and published as WO2014/126537 on 21 Aug. 2014, and which claims priority to Singapore Application No. 201301091-3, filed 13 Feb. 2013, which applications and publication are incorporated by reference as if reproduced herein and made a part hereof in their entirety, and the benefit of priority of each of which is claimed herein.

TECHNICAL FIELD

The present invention generally relates to a polymeric system for release of an active agent and a process for making the same. The disclosed polymeric system may be an injectable hydrogel for release of therapeutic agents.

BACKGROUND

A hydrogel is a network of cross-linked hydrophilic homo- or hetero-co-polymers, which has the ability to absorb and retain large amounts of water or biological fluids. Hydrogels are of great interest and high demand in industry. Natural and synthetic hydrogels have been utilized as tissue engineering matrices, wound dressings, dermal fillers and drug delivery devices. In particular, injectable hydrogels have received much attention as protein delivery systems that can form a stable depot in the body in situ and release their payloads in a sustained manner. The use of such hydrogels is desirable because it eliminates the need for surgical procedures and allows protein delivery in clinical settings.

However, there are a number of drawbacks that need to be addressed before injectable hydrogels can be efficiently used in clinical settings. For instance, conventional hydrogel systems suffer from a rapid diffusion of proteins from the hydrogel matrix due to their high permeability. Such rapid diffusion, also known as initial burst release, leads to a sudden increase in the concentration of the protein. Hence, if applied to physiological systems, problems such as undesired side effects and ineffective treatment of diseases may arise. Thus, there is a need for hydrogels that have suppressed initial burst release, such that a protein can be released over an extended period of time.

Several approaches have been developed to suppress the initial burst release and extend the release period of the proteins. However, they suffer from a number of drawbacks. At present, the most popular approach is to reduce the permeability of hydrogels by increasing the crosslinking density. However, this approach is not effective in preventing the diffusion of low molecular weight proteins. Thus, there is a need for hydrogels that are effective in preventing the diffusion of low molecular weight proteins.

Another known approach available in the art is the incorporation of heparin in the hydrogel matrices to enable the prolonged release of heparin-binding growth factors due to the specific interaction between heparin and the growth factors. However, a drawback of this approach is that these affinity hydrogel systems are only applicable to a limited range of proteins due to the need for a specific interaction between the proteins and high-affinity ligands. Thus, there is a need for an approach which is suitable for a wider range of proteins.

Another approach that has been used to suppress the initial burst release is pendant chain systems, in which proteins are directly conjugated to polymer chains of hydrogels. The conjugated proteins are released after cleavage of the linker between the proteins and polymer chains via hydrolysis or enzymatic reaction. Since chemical modification of proteins is required, changes to the bioactivity and immunogenicity of the modified proteins may arise. As such, the applicability of this approach is limited. Thus, there is a need for an approach which does not interfere with the bioactivity and immunogenicity of proteins.

There is therefore a need to provide a polymeric system that can suppress the initial burst release that overcomes, or at least ameliorates, one or more of the disadvantages described above.

SUMMARY

According to a first aspect, there is provided a polymeric system for release of an active agent, comprising a first polymeric phase containing the active agent, said first polymeric phase forming discrete regions of a set size range and being dispersed within a second polymeric phase comprising a cross-linked polymer-phenol conjugate for release of the active agent therein.

The first polymeric phase may act as a reservoir for the active agent, and entrap or release the active agent upon changes in the concentration of the active agent in the second polymeric phase. When the active agent is released from the polymeric system, the active agent in the first polymeric phase may move from the first polymeric phase to the second polymeric phase. As a result, the concentration of the active agent in the second polymeric phase advantageously remains substantially constant for prolonged periods of time.

The set size range of the discrete regions of the first polymeric phase may control the rate of release of the active agent. The set size range may be selected by controlling the rate of cross-linking of the second polymeric phase during formation of the second polymeric phase so as to form the discrete regions having the selected set size range. The rate of cross-linking may be controlled by the concentration of catalysts added to form chemical cross-links between the polymer-phenol conjugates.

This may facilitate the containment of active agents of various sizes, ranging from low to high molecular weight, and possibly more than one active agents. Notably, the discrete regions become smaller with increasing concentration of the catalyst. For example, if the gelation rate is increased, the size of the discrete regions may decrease because, the first polymeric phase (in the form of microdomains) that are dispersed in the second polymeric phase (in the form of a continuous phase) does not tend to coalesce into larger ones due to the fast gelation process. Since smaller microdomains create a smaller concentration gradient, the transport of active agents across the two polymeric phases may become slower, which in turn leads to a slower release of the encapsulated active agent from the polymeric system, leading to a sustained delivery of the active agent for a long period of time. The delivery of the active agent may be sustained for more than a month. Consequently, smaller discrete regions result in a slower release rate of the active agent from the polymeric system as compared to larger discrete regions. Advantageously, by controlling the size of the microdomains or discrete regions of the first polymeric phase, the release of the active agent(s) from the polymeric system may also be desirably controlled.

The ability to control the release of the active agent from the polymeric system via controlling the size range of the discrete regions of the first polymeric phase may allow the release of the active agent from the polymeric system without the need to use a release agent. In conventional hydrogels which require the use of a release agent, the release agent tends to diffuse out of the hydrogel into the body when applied in vivo, leading to a significant decrease in the release agent in the hydrogel, which then significantly affect the release of the active agent from the hydrogel. It is not necessary to use a release agent in the disclosed polymeric system due to the presence of the discrete regions which does not change substantially in size over time once they are formed in the body. Hence, the control of the release of the active agent from the disclosed polymeric system can be controlled over time even when placed in vivo.

In a second aspect, there is provided an injectable hydrogel for release of an active agent, comprising a first polymeric phase containing the active agent, said first polymeric phase forming discrete regions of a set size range and being dispersed within a second polymeric phase comprising a cross-linked polymer-phenol conjugate for release of the active agent therein.

In a third aspect, there is provided a carrier for delivering a biologically active substance or a drug, comprising the injectable hydrogel as described above as an active ingredient.

In a fourth aspect, there is provided a method for forming a polymeric system for release of an active agent, comprising a first polymeric phase containing the active agent, said first polymeric phase forming discrete regions of a set size range and being dispersed within a second polymeric phase comprising a cross-linked polymer-phenol conjugate for release of the active agent therein, the method comprising the steps of:

a. providing an aqueous reaction mixture comprising a first polymeric phase polymer, a polymer-phenol conjugate and an active agent; and b. controlling the rate of cross-linking of the polymer-phenol conjugate during formation of said second polymeric phase to thereby control the set size range of the discrete regions of the first polymer phase having the active agent therein.

DEFINITIONS

The following words and terms used herein shall have the meaning indicated:

The term "phase", as used in the context of the present specification, is intended to refer to a distinct, homogeneous and immiscible part of a polymeric system that may be physically separated from the rest of the polymeric system. One phase of the polymeric system may be dispersed or surrounded by a second phase, which is a continuous phase.

The word "polymer" or "polymeric" refers to a molecule having two or more monomeric repeat units. It includes linear and branched polymer structures, and also encompasses cross-linked polymers as well as copolymers (which may or may not be cross-linked), thus including block copolymers, alternating copolymers, random copolymers, and the like. A "polymer-phenol conjugate" refers to a polymer covalently attached to a phenol-containing moiety, as defined herein.

The term "domain" or "microdomain" herein refers to discrete regions of a set size range in the polymeric system.

The term "cross-linked" herein refers to a reaction between two moieties, an example being an oxidative coupling of tyramine moieties catalyzed by an agent and an oxidant.

As used herein, polyethylene glycol or "PEG" broadly refers to a linear, multi-arm, or branched polymer backbone comprising a water-soluble and non-peptidic polymer having repeat $CH_2CH_2O$ units. The PEG family of polymers generally exhibits the properties of solubility in water and in many organic solvents, lack of toxicity, and lack of immunogenicity. The term PEG should be understood to be inclusive and to include polyethylene glycol in any of its linear, branched or multi-arm forms, including alkoxy PEG, bifunctional PEG, forked PEG, branched PEG, pendant PEG, and PEG with degradable linkages therein.

PEG, in any of the forms described herein; is typically clear, colorless, odorless, soluble in water, stable to heat, inert to many chemical agents, does not hydrolyze or deteriorate (unless specifically designed to do so), and is generally nontoxic. PEG is considered to be biocompatible, which is to say that PEG is capable of coexistence with living tissues or organisms without causing harm. More specifically, PEG is substantially non-immunogenic, which is to say that PEG does not tend to produce an immune response in a patient. When attached to a molecule having some desirable function in the body, such as a biologically active agent, the PEG tends to mask the agent and can reduce or eliminate any immune response so that an organism can tolerate the presence of the agent. PEG-containing conjugates and hydrogels tend not to produce a substantial immune response or cause clotting or other undesirable effects.

The term "hydrogel" is used in the conventional sense to refer to a water-swellable polymeric system that can absorb a substantial amount of water to form an elastic gel, wherein the "system" comprises a first polymeric phase containing the active agent, the first polymeric phase forming discrete regions of a set size range and being dispersed within a second polymeric phase.

The term "gelation rate" is used herein to refer to the rate of cross-linking of the second polymeric phase during formation of the second polymeric phase so as to form the discrete regions having the selected set size range.

The term "stiffness" is used herein to refer to the rigidity of the polymeric system. The rigidity is defined as the extent to which the polymeric system resists deformation in response to an applied force.

The term "storage modulus" is used herein as an indicator that characterizes the stiffness of the polymeric system. The storage modulus is the tendency of the polymeric system to be deformed elastically when a force is applied to it.

The term "active agent" is used herein to refer to a chemical material or compound suitable for administration to a human patient and that induces a desired beneficial effect, e.g., exhibits a desired pharmacological activity. The term includes, for example, agents that are therapeutically effective, prophylactically effective, and cosmetically (and cosmeceutically) effective. Also included are derivatives and analogs of those compounds or classes of compounds specifically mentioned which also induce the desired beneficial effect. The active agent may be selected from the group consisting of proteins, antibodies, peptides, small-molecule drugs, nucleic acid-based drugs, nanoparticulate systems and mixtures thereof.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF OPTIONAL EMBODIMENTS

Exemplary, non-limiting embodiments of a polymeric system for release of an active agent will now be disclosed. The polymeric system comprises a first polymeric phase containing the active agent, said first polymeric phase forming discrete regions of a set size range and being dispersed within a second polymeric phase comprising a cross-linked polymer-phenol conjugate for release of the active agent therein.

The first polymeric phase may act as a reservoir for the active agent, and entrap or release the active agent upon changes in the concentration of the active agent in the second polymeric phase. When the active agent is released from the polymeric system, the active agent in the first polymeric phase may move from the first polymeric phase to the second polymeric phase. As a result, the concentration of the active agent in the second polymeric phase advantageously remains substantially constant for prolonged periods of time. This advantageously helps in the sustained release of the active agent from the polymeric system.

The first polymeric phase may comprise a polymer selected from the group consisting of polyether, polyamine, polyester, polyacetals, poly(amino acids), polysaccharides, polynucleotides, polypeptides, polyanhydride, polyorthoester, polyurethane, polyamide, polyaliphatic, polyaromatic, polycarbonate, and combinations thereof.

The polymer may be selected from the group consisting of polyethyleneglycol (PEG), poly(propylene glycol), poly(2-ethyl-2-oxazoline), polyethylenimine, poly(methacrylic acid), poly(vinyl alcohol), polyvinylpyrrolidone, polyallylamine, poly(styrenesulfonic acid), hydroxypropyldextran, hydroxyethyl cellulose, methyl cellulose, Ficoll, Pluronic F68, nonylphenol polyoxyethylene 20, Zonyl, and combinations thereof.

The average molecular weight of the polymers in the first polymeric phase may be in the range of about 1,000 to about 2,000,000, about 1,000 to about 10,000, about 1,000 to about 50,000, about 1,000 to about 75,000, about 1,000 to about 1000,000, about 100,000 to about 200,000, about 100,000 to about 300,000, about 100,000 to about 400,000, about 100,000 to about 500,000, about 100,000 to about 600,000, about 100,000 to about 700,000, about 100,000 to about 800,000, about 100,000 to about 900,000, about 100,000 to about 1,000,000, about 100,000 to about 1,500,000, or about 100,000 to about 2,000,000. The average molecular weight of the polymers in the first polymeric phase is preferably in the range of about 1,000 to about 100,000.

The set size range of the discrete regions of the first polymeric phase may control the rate of release of the active agent. The set size range may be selected by controlling the rate of cross-linking of the second polymeric phase during formation of the second polymeric phase so as to form the discrete regions having the selected set size range.

The size of the discrete regions may be in the micron-range or the nano-range. The range of the size of the discrete regions may be selected from the group consisting of: about 1 μm to about 150 μm, about 1 μm to about 10 μm, about 1 μm to about 20 μm, about 1 μm to about 30 μm, about 1 μm to about 40 μm, about 1 μm to about 50 μm, about 1 μm to about 60 μm, about 1 μm to about 70 μm, about 1 μm to about 80 μm, about 1 μm to about 90 μm, about 1 μm to about 100 μm, about 50 μm to about 150 μm, about 10 μm to about 150 μm, about 20 μm to about 150 μm, about 30 μm to about 150 μm, about 40 μm to about 100 μm, about 60 μm to about 150 μm, about 70 μm to about 150 μm, and about 5 μm to about 100 μm. The preferred size of the set size range of the discrete regions may be from about 1 μm to about 100 μm.

The discrete regions may form microdomains, microspheres or microcapsules in the second phase. Advantageously, these microdomains, microspheres or microcapsules may encapsulate or trap active agents.

The microdomains may encapsulate or trap active agents of various sizes, ranging from low to high molecular weight, and possibly more than one active agents The molecular weight of the active agent may be in the range of about 1 to about 600 kDa. The range of the molecular weight of the active agent may be selected from the group consisting of: about 1 kDa to about 50 kDa, about 1 kDa to about 100 kDa, about 1 kDa to about 200 kDa, about 1 kDa to about 300 kDa, about 1 kDa to about 400 kDa, about 1 kDa to about 500 kDa, about 50 kDas to about 100 kDa, about 50 kDa to about 200 kDa, about 50 kDa to about 300 kDa, about 50 kDa to about 400 kDa, about 100 kDa to about 500 kDa, and about 1 kDa to about 600 kDa. kDa Notably, the discrete regions may become smaller with increasing concentration of a catalyst. For example, if the gelation rate is increased, the size of the discrete regions may decrease because the microdomains dispersed in the second polymeric phase do not tend to coalesce into larger ones due to the fast gelation process. Since smaller microdomains create a smaller concentration gradient, the transport of active agents across the two polymeric phases may become slower, which in turn leads to a slower release of the encapsulated active agent from the polymeric system. Consequently, smaller discrete regions may result in a slower release rate of the active agent from the polymeric system as compared to larger discrete regions, leading to a sustained delivery of the active agent for a long period of time. The delivery of the active agent may be sustained for more than a month. The delivery of the active agent may be sustained for a duration selected from the group consisting of: about 1 month, about 2 months, about 3 months, about 4 months, about 6 months, about 8 months, about 10 months, about 12 months, about 18 months and about 24 months.

The second polymeric phase may comprise a cross-linked polymer-phenol conjugate. By controlling the rate of cross-linking of the polymer-phenol conjugate, the drug release kinetics may be controlled. The drug release kinetics may be regulated by changing the size of microdomains through controlling the cross-linking rate. The second polymeric phase may be formed by utilizing an agent that controls the rate of cross-linking during formation of the second polymeric phase to thereby control the set size range of the discrete regions of the first polymer phase.

The cross-linked polymer-phenol conjugate may be a cross-linked polysaccharide-phenol conjugate or a cross-linked protein-phenol conjugate. The polymer-phenol conjugate may be a polymer-phenol containing conjugate. Suitable polysaccharides include, but are not limited to, dextran polymer, chitosan, chitin, cellulose, starch, glycogen, alginate, carrageenan, Ficoll, gellan, guar gum, hyaluronic acid, heparin, methylcellulose, pectin, polysucrose, pullulan, scleroglucan, xanthan, and xyloglucan.

Suitable dextran polymers include, but are not limited to methacrylated dextran (dexMA), hydroxyethylmethacrylated dextran (dexHEMA), hydroxyethylmethacrylated dextran-lactate (dexLactateHEMA), dextran sulphate, hydroxypropyldextran, and cyclodextrin-dextran conjugate.

The degree of substitution of the dextran polymer may be from 1 to 30. The degree of substitution can be a value selected from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30.

The average molecular weight of the polymers in the second polymeric phase may be in the range of about 1,000 to about 10,000, about 1,000 to about 50,000, about 1,000 to about 75,000, about 1,000 to about 1000,000, about 100,000 to about 200,000, about 100,000 to about 300,000, about 100,000 to about 400,000, about 100,000 to about 500,000, about 100,000 to about 600,000, about 100,000 to about 700,000, about 100,000 to about 800,000, about 100,000 to about 900,000, about 100,000 to about 1,000,000, about 100,000 to about 1,500,000, or about 100,000 to about 2,000,000. The average molecular weight of the polymers in the second polymeric phase is preferably in the range of about 10,000 to about 1,500,000.

The phenol in the polymer-phenol conjugate may be a phenol-containing moiety. The phenol-containing moiety may include, but are not limited to tyramine, tyrosine, hydroxyphenylacetic acid, 3-(4-Hydroxyphenyl)propionic acid, catechin, epicatechin gallate, epigallocatechin, epigallocatechin gallate (EGCG), gallocatechin, gallocatechin gallate, dihydroxyphenylalanine, dopamine, norepinephrine, tannin, tannic acid, gallic acid, pyrogallol, pyrrole, derivatives thereof, and a combination thereof.

The polymer-phenol conjugate may be dextran-tyramine conjugate or gelatin-phenol conjugate. In the dextran-tyramine conjugate, tyramine serves as a cross-linking moiety such that the polymeric system is formed by a cross-linking reaction between the tyramine molecules. Tyramine, being one of the simplest hydroxyphenol compounds, has a primary amine group that allows for facile conjugation to polymers. Tyramine also has good solubility in water and physiological buffer solutions.

To form the polymeric system, an aqueous solution of the polymer-phenol conjugate may be first mixed with the aqueous solution of the polymer of the first polymeric phase. This is followed by an enzymatic cross-linking reaction of the polymer-phenol conjugates by using a catalyst and an oxidant. The rate of the enzymatic cross-linking reaction may be controlled by controlling the amount of the catalyst that facilitates oxidation reactions of the tyramine moiety, which in turn affects the gelation rate of the polymer-tyramine conjugate, leading to the control of the size of the microdomains and hence release rate of the active agent.

The time taken for the formation of the polymeric system increases with reducing the concentration of the catalyst. This is attributed to the slower rate of cross-linking at lower concentrations of the catalyst. Although the gelation rate is different, the storage modulus of the polymeric system may be substantially unaffected. As such, the gelation rate can be tuned by changing the concentration of the catalyst, while maintaining the stiffness of the polymeric system.

The agent that controls the rate of cross-linking during polymerization is a catalyst. The concentration of the catalyst is changed in order to control the rate of cross-linking between the phenol moieties (or phenol-containing moieties), of the polymer-phenol conjugate. Suitable catalysts include, but are not limited to, horseradish peroxidase, human myeloperoxidase, lactoperoxidase, eosinophil peroxidase, thyroid peroxidase, prostaglandin H synthases, soybean peroxidase, hemin, hematin, microperoxidase-11, and cytochrome c. The concentration of the catalyst may be changed in order to control the rate of cross-linking. The range of the concentration of the catalyst may be selected from the group consisting of about 0.01 units/mL to about 0.50 units/mL, such as about 0.01 units/mL, about 0.02 units/mL, about 0.05 units/mL, about 0.07 units/mL, about 0.10 units/mL, about 0.13 units/mL, about 0.15 units/mL, about 0.17 units/mL, about 0.19 units/mL, about 0.21 units/mL, about 0.25 units/mL, about 0.30 units/mL, about 0.35 units/mL, about 0.40 units/mL, about 0.43 units/mL, about 0.45 units/mL, and about 0.50 units/mL.

The concentration of the agent may be changed in order to control the rate of cross-linking. The rate of release of the active agent from the polymeric system is dependent on the size of the discrete regions. Advantageously, smaller discrete regions result in a slower release rate of the active agent from the polymeric system as compared to larger discrete regions. The release rate of the active agent (that is, the percentage of loaded active agent that can be released from the polymeric system) from the polymeric system is 0.5% to 20% per day, such as 0.5%, 1%, 2%, 3%, 4%, 5%, 6%, 7%, 8%, 9%, 10%, 11%, 12%, 13%, 14%, 15%, 16%, 17%, 18%, 19% and 20% per day.

An advantage of the disclosed polymeric system from conventional drug release systems is that it allows for active agents to be incorporated into a polymeric system via preferential partitioning, which allows for the controlled incorporation and release of a variety of different active agents from the polymeric system.

The first polymeric phase and second polymeric phase are immiscible phases when mixed at appropriate concentrations. This aqueous two-phase polymeric system advantageously prevents the initial burst release of the active agent by preferential partitioning of the active agent(s) in the first polymeric phase. The extent and outcome of preferential partitioning may be controlled by the nature of the active agent(s), the molecular weight and concentration of the polymers making up the first and second polymeric phases, and the ionic composition of the phases. The concentration of the polymers may be in the range of about 1% (w/v) to about 50% (w/v), about 5% (w/v) to about 50% (w/v), about 10% (w/v) to about 50% (w/v), about 20% (w/v) to about 50% (w/v), about 30% (w/v) to about 50% (w/v), about 40% (w/v) to about 50% (w/v). The ionic composition of the phases may be selected from the group consisting of sodium phosphate, sodium chloride, sodium acetate, sodium citrate, sodium malonate, sodium nitrate, sodium succinate, sodium sulfate, potassium chloride, ammonium acetate, ammonium chloride, ammonium nitrate and ammonium sulfate.

The active agent may be selected from the group consisting of proteins, antibodies, peptides, small-molecule drugs, nucleic acid-based drugs, nanoparticulate systems and mixtures thereof.

The active agent may be selected from the group consisting of insulin, bovine serum albumin and interferon.

The active agent may be conjugated to a polymer that preferentially partitions to the first polymeric phase as compared to the second polymeric phase. The two polymeric phases may be immiscible when mixed at appropriate concentrations. The concentration of the polymers may be in the range of about 1% (w/v) to about 50% (w/v), about 5% (w/v) to about 50% (w/v), about 10% (w/v) to about 50% (w/v), about 20% (w/v) to about 50% (w/v), about 30% (w/v) to about 50% (w/v), about 40% (w/v) to about 50% (w/v). The partitioning behavior is governed by the entropy of mixing the active agent and polymer, which largely depends on the nature of the partitioned active agent, the molecular weight and concentration of the phase polymers, or the ionic composition of the phases.

Greater than 20% of said conjugated-active agent may be present in the first polymeric phase as compared to said second polymeric phase. The percentage of said conjugated-active agent present in the first polymeric phase may be selected from the group consisting of: 20%, 25%, 30%, 35%, 40%, 45%, 50%, 55%, 60%, 65%, 70%, 75%, 80%, 85%, 90% and 95%.

The conjugated-active agent may be a PEG conjugated-active agent. Advantageously, the active agent can be preferentially partitioned in the PEG microdomains such that the PEG microdomains may act as a drug reservoir which releases the protein drugs upon changes in the drug concentration in the second polymeric phase. In one embodiment, the PEG conjugated-active agent may be selected from the group consisting of PEGinterferon alpha-2a (PEGASYS), PEGylated L-asparaginase (Oncaspar), PEG-adenosine deaminase (Adagen), PEGinesatide (Omontys), PEGylated uricase (Pegloticase), PEGylated hyaluronidase, PEGylated epidermal growth factor, PEGylated tumor necrosis factor, PEGylated tumor necrosis factor-related apoptosis-inducing ligand (PEG-TRAIL), certolizumab pegol (Cimzia), PEGylated erythropoetin (Mircera), PEGaptanib (Macugen), PEGylated recombinant methionyl human granulocyte colony-stimulating factor (Neulasta), PEG-human growth hormone mutein antagonists (Somavert) and PEGylated interferon alpha-2b (Pegintron).

The polymeric system for release of an active agent as disclosed herein, may find application in drug delivery or tissue engineering scaffolds to promote tissue repair and/or regeneration. They may be useful in other materials in related applications where controlled release of multiple active agents is desired, e.g. biosensors, detoxification, DNA delivery, etc.

Exemplary, non-limiting embodiments of an injectable hydrogel for release of an active agent will now be disclosed. The injectable hydrogel may comprise a first polymeric phase containing the active agent, the first polymeric phase forming discrete regions of a set size range and being dispersed within a second polymeric phase comprising a cross-linked polymer-phenol conjugate for release of the active agent therein.

It was advantageously discovered that radiation was not required to initiate the cross-linking reaction required to form a hydrogel and that the hydrogel may be formed in situ. The use of injectable in situ forming hydrogels eliminates the need for surgical procedures, which would otherwise have been required to implant pre-formed hydrogels.

The hydrogel may exhibit sustained release of the active agent due to the reduction of initial burst release. A slower release may be observed with smaller discrete regions. More advantageously, the size of the discrete regions can be controlled by the gelation rate of the second polymeric phase.

The hydrogel may also include conventional additives such as fillers, preservatives, pH regulators, softeners, thickeners, pigments, dyes, refractive particles, stabilizers, toughening agents, detackifiers, pharmaceutical agents, anti-adhesion barriers, wound sprays and permeation enhancers.

Exemplary, non-limiting embodiments of a carrier for delivering a biologically active substance or a drug, comprising the injectable hydrogel as described above will now be disclosed.

The carrier allows for sustained release of the biologically active substance or drug over a period of time due to the reduction of the initial burst release. The release rate of the biologically active substance or drug may be tuned by the size of the discrete regions of the polymeric system.

The carrier can be used for localized delivery of one or more, biologically active substance or drug to a particular target location, thereby facilitating the treatment of an illness or disease.

Exemplary, non-limiting embodiments of a method for forming a polymeric system for release of an active agent will now be disclosed. The polymeric system, comprising a first polymeric phase containing the active agent, the first polymeric phase forming discrete regions of a set size range and being dispersed within a second polymeric phase comprising a cross-linked polymer-phenol conjugate for release of the active agent therein, the method comprising the steps of:

a. providing an aqueous reaction mixture comprising a first polymeric phase polymer, a polymer-phenol conjugate and an active agent; and b. controlling the rate of cross-linking of the polymer-phenol conjugate during formation of the second polymeric phase to thereby control the set size range of the discrete regions of the first polymer phase having the active agent therein.

The method further comprises the step of adding an agent that controls the rate of cross-linking of said second polymeric phase to the reaction mixture. Advantageously, this leads to control of the size of the discrete regions.

The method further comprises the step of selecting the concentration of the agent to thereby control the rate of cross-linking of the second polymeric phase.

The cross-linking step involves the formation of a C—C bond or C—O bond between a pair of polymer-phenol conjugates. Advantageously, the cross-linking step may be fast and efficient. The time taken for cross-linking is typically from 1 to 60 minutes. Suitable time taken for cross-linking may be a value selected from the group consisting of: 1 minute, 5 minutes, 10 minutes, 15 minutes, 20 minutes, 25 minutes, 30 minutes, 35 minutes, minutes, 45 minutes, 50 minutes, 55 minutes and 60 minutes. The cross-linking may be carried out at a temperature of 4° C. to 40° C. The temperature for cross-linking can be a value selected from the group consisting of: 4° C., 5° C., 10° C., 15° C., 20° C., 25° C., 30° C., 31° C., 32° C., 33° C., 34° C., 35° C., 36° C., 37° C., 38° C., 39° C., and 40° C. The method further comprises the step of adding an oxidizing agent to the reaction mixture.

The method further comprises the step of adding an agent that controls the rate of cross-linking to the reaction mixture. The agent may be a catalyst. Suitable catalysts include an enzyme selected from the group consisting of horseradish peroxidase, glutathione peroxidase, haloperoxidase, catalase, human myeloperoxidase, myeloperoxidase, peroxide, peroxiredoxin, vanadium bromoperoxidase, lactoperoxidase, eosinophil peroxidase, thyroid peroxidase, prostaglandin H synthases, soybean peroxidase, hemin, hematin, microperoxidase-11, and cytochrome c.

Suitable oxidizing agents may include a peroxide selected from the group consisting of hydrogen peroxide, sodium peroxide, potassium peroxide, hydrogen superoxide, potassium superoxide, alkyl peroxides, aryl peroxides, acyl peroxides, organic hydroperoxides, organic peracids, sodium percarbonate, ammonium persulfate and perborates.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 6a is an image of a dextran-tyramine/PEG hydrogel using 0.21 units/mL HRP. FIG. 6b is an image of a dextran-tyramine/PEG hydrogel using 0.32 units/mL HRP. FIG. 6c is an image of a dextran-tyramine/PEG hydrogel using 0.43 units/mL HRP. FIG. 6d is an image of a dextran hydrogel using 0.21 units/mL HRP.

DETAILED DESCRIPTION OF DRAWINGS

Figure 1:
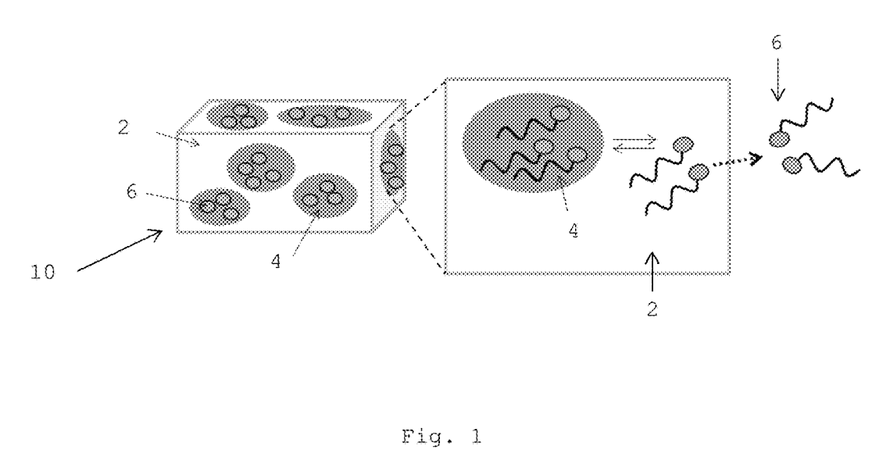
FIG. 1 is a schematic illustration depicting the polymeric system for release of an active agent, comprising a first polymeric phase and a second polymeric phase.

FIG. 1 is a schematic illustration depicting the polymeric system 10 for release of an active agent 6, comprising a first polymeric phase 4 containing the active agent 6, the first polymeric phase 4 forming discrete regions of a set size range and being dispersed within a second polymeric phase 2 comprising a cross-linked polymer-phenol conjugate for release of the active agent 6 which is encapsulated by the first polymeric phase 4. The polymer that makes up the first polymeric phase 4 acts as a reservoir for active agent 6 due to the preferential partitioning of the active agent 6 in the first polymeric phase 4. Consequently, initial burst release is prevented because diffusion of the active agent 6 from the first polymeric phase 4 will only occur when the concentration of the active agent 6 in the second polymeric phase 2 decreases. This decrease in concentration of the active agent 6 in the second polymeric phase 2 occurs when the polymeric system 10 releases the active agent 6. As a result of the replenishing of the active agent 6 in the second polymeric phase 2, the concentration of the active agent 6 remains nearly constant.

Figure 2:
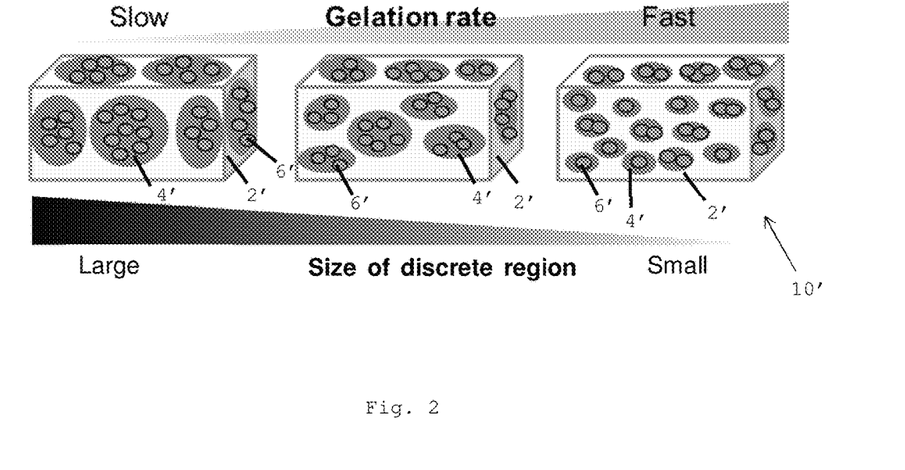
FIG. 2 is a schematic representation showing the correlation of the rate of formation of the polymeric system and the size of the discrete regions of the first polymeric phase.

FIG. 2 is a schematic representation showing the correlation of the gelation rate and the size of the discrete regions of the first polymeric phase 4' in the second polymeric phase 2'. Here, like numbers are used to describe like features but with a prime symbol. It is possible to regulate the release of the active agent 6' from the polymeric system 10' by changing the size of the discrete regions of the first polymeric phase 4' through the control of the gelation rate. For example, if the gelation rate is increased, the size of the discrete regions of the first polymeric phase 4' may decrease because the discrete regions of the first polymer phase 4' dispersed in the second polymeric phase 2' do not tend to coalesce into larger discrete regions due to the fast gelation process. Since smaller discrete regions of the first polymer phase 4' create a smaller concentration gradient, the transport of the active agent 6' across the first polymeric phase 4' and second polymeric phase 2' may become slower, which in turn leads to a slower release of the encapsulated active agent 6'. In this way, the release rate of the active agent 6' can be controlled by changing the size of the discrete regions of the first polymeric phase 4'.

EXAMPLES

Non-limiting examples of the invention and a comparative example will be further described in greater detail by reference to specific Examples, which should not be construed as in any way limiting the scope of the invention.

Materials Used for all the Examples

Dextran ($M_w$=500 kDa), polyethylene glycol. (PEG, $M_w$=10 kDa), tyramine, 4-nitrophenyl chloroformate (PNC), dimethyl sulfoxide (DMSO), pyridine, dextranase and fluorescein isothiocyanate (FITC)-labeled bovine serum albumin (FITC-BSA) were purchased from Sigma-Aldrich (Minnesota, USA). PEG-succinimidyl propionate (PEG-SPA, $M_w$=5 kDa) was obtained from Nektar Therapeutics (California, USA). Horseradish peroxidase (HRP, 190 units mg-1) was purchased from Wako Pure Chemical Industries (Osaka, Japan). Hydrogen peroxide ($H_2O_2$) was obtained from Lancaster Synthesis (Lancashire, UK). Interferon alpha-2a (IFN-α2a) was purchased from Santa Cruz biotechnology (California, USA). PEGylated IFN-α2a (PEGASYS), PEGylated epoetin beta (Mircera) and PEGylated granulocyte colony-stimulating factor (Neulastim) were obtained from Roche (Basel, Switzerland). Human interferon-alpha ELISA kit obtained from PBL InterferonSource (New Jersey, USA), erythropoietin ELISA kit obtained from Abcam (Cambridge, UK) and G-CSF/CSF3 ELISA kit obtained from Sigma-Aldrich (Minnesota, USA) were used according to the manufacturer's instructions. All other chemicals were of analytical grade. Protein LoBind microcentrifuge tube was obtained from Eppendorf (Hamburg, Germany).

Example 1

Synthesis of a Polymer-Phenol Conjugate

A dextran-tyramine conjugate was synthesized by dissolving dextran (5 g, 92.36 mmol OH) in a 100 mL mixture of DMSO/pyridine (1:1, v/v). After the dextran solution was cooled at 4° C., PNC (1.1 g, 5.46 mmol) was slowly added. The reaction mixture was stirred for 24 hours at 4° C. After the solution was poured into cold ethanol, the precipitate was washed with cold ethanol and diethyl ether, and then dried in a vacuum oven at 25° C. The dried dextran-PNC conjugate (1 g, 0.37 mmol PNC) was dissolved in 70 mL of DMSO. To this solution, tyramine (35 mg, 0.25 mmol) was added to initiate the conjugation reaction. The mixture was stirred for 24 hours at 25° C. Then, the solution was added dropwise to cold deionized water (200 mL) while stirring. The resultant dextran-tyramine conjugate was transferred to dialysis tubes with a molecular weight cutoff of 3,500 Da. The tubes were dialyzed against deionized water. The purified solution was lyophilized to obtain the dextran-tyramine conjugate.

The structure of the dextran-tyramine conjugate was confirmed by $^1H$ NMR spectroscopy. The dried dextran-tyramine conjugate (10 mg) was dissolved in 0.7 mL $D_2O$ and then examined by a Bruker $^1H$ NMR spectrometer operating at 400 MHz. The degree of substitution (DS) is defined as the number of substituents per 100 anhydroglucose units in dextran. DS was determined to be 6 by comparing the relative peak area of four protons on a tyramine phenyl ring (6.86 ppm and 7.17 ppm) and anomeric protons (5.00 ppm and 5.35 ppm) in dextran.

Example 2

Analysis of Partition of Proteins in a Dextran-Tyramine/PEG Two-Phase Solution

Dextran and PEG were dissolved in 10 mM phosphate-buffered saline (PBS, pH 7.4) at a concentration of 10% (w/v) and 30% (w/v), respectively. To determine the partition coefficient of protein, 270 µL of dextran solution, 30 µL of PEG solution and 12 µL of protein solution were mixed in a Protein LoBind microcentrifuge tube. Tested proteins are listed as follows: IFN-α2a (0.72 µg/mL), PEGASYS (2.16 µg/mL), erythropoietin (2 IU/mL), Mircera (3.33 µg/mL), granulocyte colony-stimulating factor (10 ng/mL) and Neulastim (1 µg/mL). The mixture was left to settle for 1 hour at 4° C. to induce phase separation. The protein concentrations in the upper (PEG) and lower (dextran) phases were measured by using the corresponding ELISA kit. The partition coefficient was determined by dividing the protein concentration in PEG phase with the protein concentration in dextran phase.

To analyze the partition coefficient of albumin and PEGylated albumin, 270 µL of dextran solution, 30 µL of PEG solution and 12 µL of FITC-BSA (10 mg/mL) or PEGylated FITC-BSA (10 mg/mL) solution were mixed in a Protein LoBind microcentrifuge tube. The mixture was left to settle for 1 hour at 4° C. to induce phase separation. The concentration of proteins in the PEG and dextran phases was assessed by measuring the fluorescence of FITC dye at an emission wavelength of 520 nm using a microplate reader (Tecan Group Ltd., Switzerland). The partition coefficient is determined by dividing the protein concentration in PEG phase with the protein concentration in dextran phase.

Figure 3:
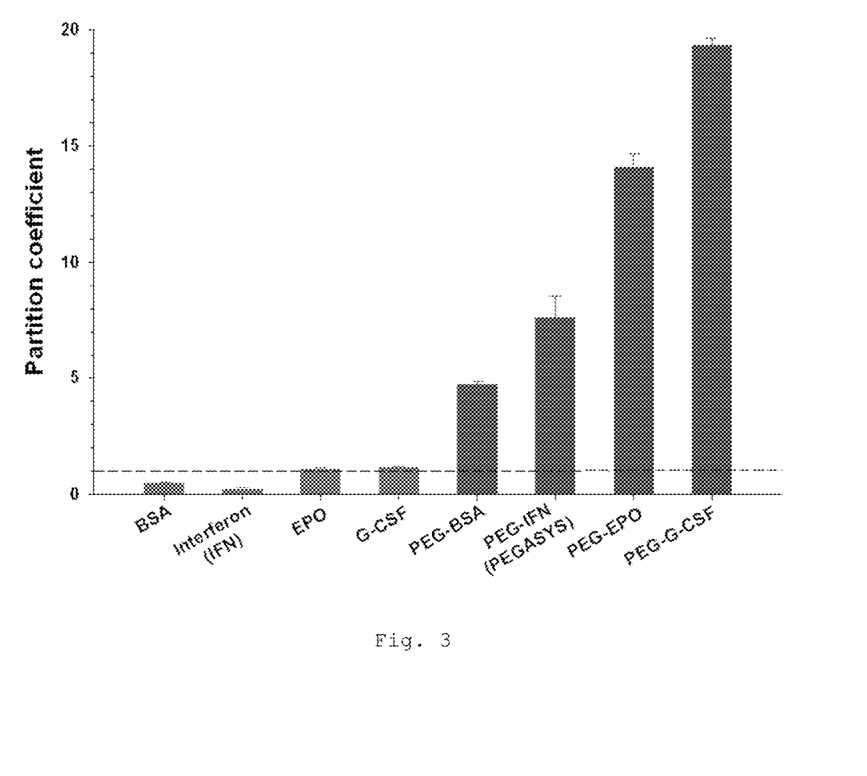
FIG. 3 is a bar graph depicting the partition coefficients of various active agents in the polymeric system. The dotted line indicates a partition coefficient of 1. Values above the dotted line indicate preferential partitioning of the active agents in the PEG phase, while the values below the line indicate preferential partitioning of the active agents in the dextran phase.

As shown in FIG. 3, the concentrations of bovine serum albumin, interferon, EPO and G-CSF in PEG phase were similar to those in the dextran phase. The observed partition behaviors were consistent with the previous reports, in which most kinds of proteins favor more in dextran phase. In contrast, all the PEGylated proteins were distributed mainly in PEG phase. The concentration of PEGASYS in PEG phase was significantly higher than that in dextran-tyramine phase, indicating that PEGASYS was preferentially partitioned into PEG phase. Therefore, it is conceivable that the PEG microdomains can serve as a universal drug reservoir for all types of PEGylated proteins.

Example 3

Formation and Characterization of Dextran-Tyramine/PEG Hydrogels with Phase-Separated Structure Dextran-tyramine conjugate and PEG were dissolved in mM PBS solution (pH 7.4) at a concentration of 10% (w/v) and 30% (w/v), respectively. Typically, 270 µL of dextran-tyramine solution, 30 µL of PEG solution and 6 µL of deionized water were mixed in a microcentrifuge tube. Subsequently, 3 µL of HRP and 3 µL of $H_2O_2$ solution in varying concentrations were added. The mixture was immediately vortexed and 210 µL of the resultant mixture was applied to the bottom plate of a HAKKE Rheoscope 1 rheometer (Karlsruhe, Germany). Rheological measurement was carried out at 37° C. using a cone and plate geometry of 3.5 cm diameter and 0.949° cone angle. The evolution of storage modulus (G') and loss modulus (G") was monitored as a function of time. For comparison, dextran-tyramine hydrogels were prepared using 30 µL of deionized water instead of PEG solution.

Figure 4:
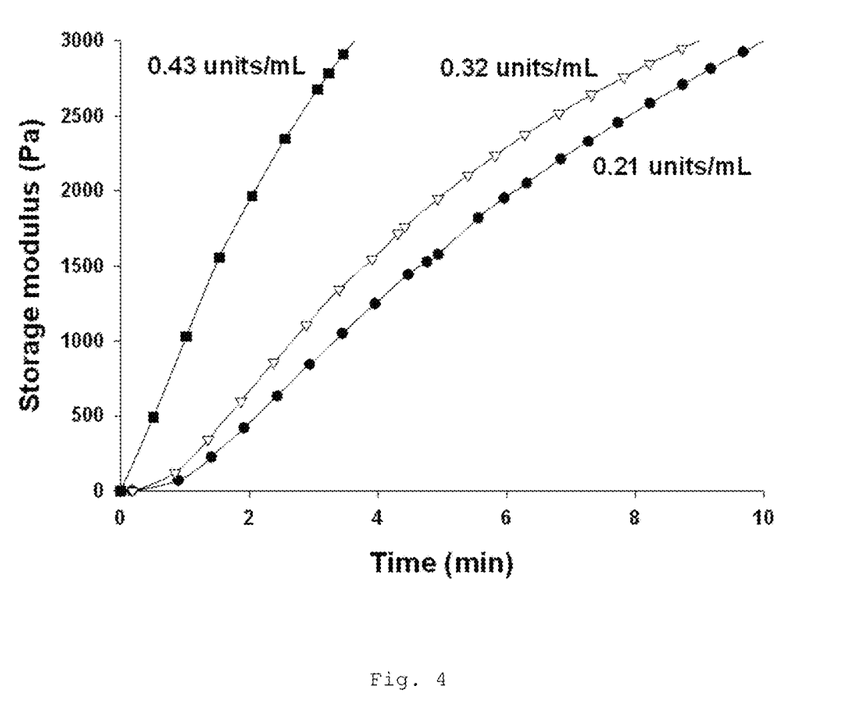
FIG. 4 shows the time course of changes in the storage modulus of the polymeric system 10 with varying concentrations of catalyst.

In general, the gelation rate of dextran-tyramine/PEG hydrogels was found to be tunable with varying concentrations of HRP. FIG. 4 shows the time course of changes in the storage modulus of dextran-tyramine/PEG hydrogels prepared with different concentrations of HRP. When HRP was added at a concentration of 0.43 units/mL, the formation of the dextran-tyramine/PEG hydrogels occurred rapidly; the cross-linking reaction was complete within 15 minutes. It was also observed that the gelation rate gradually decreased with reducing the HRP concentration. This phenomenon was attributed to the slower coupling reaction of tyramine moieties at lower concentrations of HRP.

Figure 5:
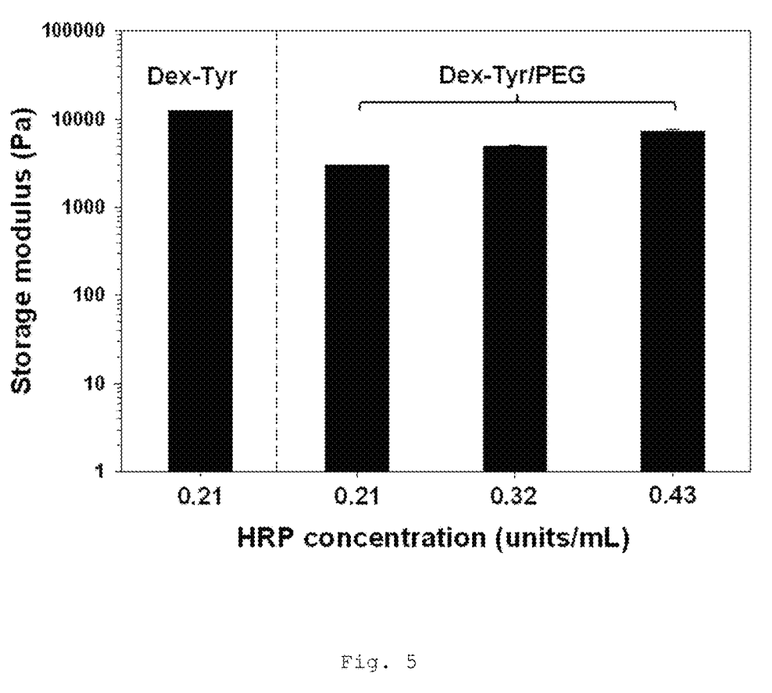
FIG. 5 is a bar graph depicting the storage modulus of polymeric systems with one polymeric phase and two polymeric phases as a function of concentration of catalyst.

Although the gelation rate was different, the storage modulus of the dextran-tyramine/PEG hydrogels became similar eventually (FIG. 5). Hence, these results revealed that the gelation rate of dextran-tyramine/PEG hydrogels could be tuned by changing the HRP concentration, while maintaining their stiffness. This ability of the disclosed polymeric system to control the size of PEG microdomains without affecting its stiffness makes it superior to dextran-methacrylate/PEG hydrogels. Since a radical polymerization is used to produce dextran-methacrylate/PEG hydrogels, a significant change in the gel stiffness is inevitable when controlling the PEG domain structures. This implies that the hydrophilic nature and biocompatibility of dextran-methacrylate/PEG hydrogels are significantly changed when controlling the PEG domain structures.

In contrast, the dextran-tyramine/PEG hydrogel disclosed herein is an enzymatically cross-linked hydrogel system of which the stiffness and gelation rate is independently tuned by changing the concentrations of $H_2O_2$ and HRP, respectively. As shown from FIG. 5, the disclosed polymeric system can regulate the size of PEG microdomains without significantly affecting its stiffness.

Figure 6:
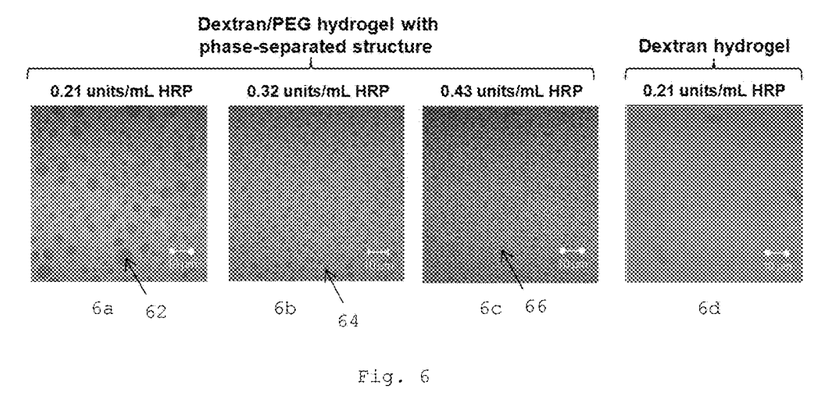
FIG. 6 are confocal microscope images depicting the discrete regions in the polymeric system with varying concentrations of catalyst. It can be seen that the PEG microdomain 62 is larger than PEG microdomains 64 and 66 because a lower concentration of HRP is used. As such, a lower concentration of HRP leads to larger microdomains.

The structure of PEG microdomains of the hydrogels was examined using a confocal laser scanning microscope. Dextran-tyramine/PEG hydrogels were formed on a glass-bottom microwell dish (MatTek Corporation, USA) and then observed by using a confocal laser scanning microscope (Zeiss LSM 5 DUO). Rhodamine-labeled PEG and FITC-labeled dextran were used to visualize PEG and dextran phases, respectively. The diameter of the PEG microdomains was determined by measuring more than 50 microdomains with an Image-Pro Plus software (Media Cybernetics, USA). The scale bar represents 10 micrometers. As illustrated in FIG. 6, round PEG microdomains were observed to be dispersed throughout the dextran-tyramine network, as exemplified by PEG microdomains 62, 64 and 66. The disclosed polymeric system offers more sophisticated control over the size of PEG microdomains than dextran-methacrylate/PEG hydrogels. As shown in FIG. 6, the PEG microdomains of the disclosed polymeric system are more spherical and uniform than dextran-methacrylate/PEG hydrogels. In the case of dextran-methacrylate/PEG hydrogels, 40 wt. % methacrylic dextran and 40 wt. % PEG solution are mixed together before radical polymerization. Since 40 wt. % methacrylic dextran and 40 wt. % PEG solution are immiscible, a heterogeneous dextran-methacrylate/PEG mixture is formed. This leads to the formation of irregular and heterogeneous PEG domains.

In comparison, 10 wt. % dextran-tyramine and 30 wt. % PEG solution are mixed together before enzymatic cross-linking reaction to form the disclosed dextran-tyramine/PEG hydrogels. A homogeneous mixture is formed because 10 wt. % dextran-tyramine and 30 wt. % PEG solution are miscible. As a result, the disclosed polymeric system advantageously results in the formation of spherical and highly monodisperse PEG domains. Notably, the PEG microdomains became smaller with increasing HRP concentration. In the case of dextran-tyramine hydrogels without PEG, no microdomain structures were observed.

Figure 7:
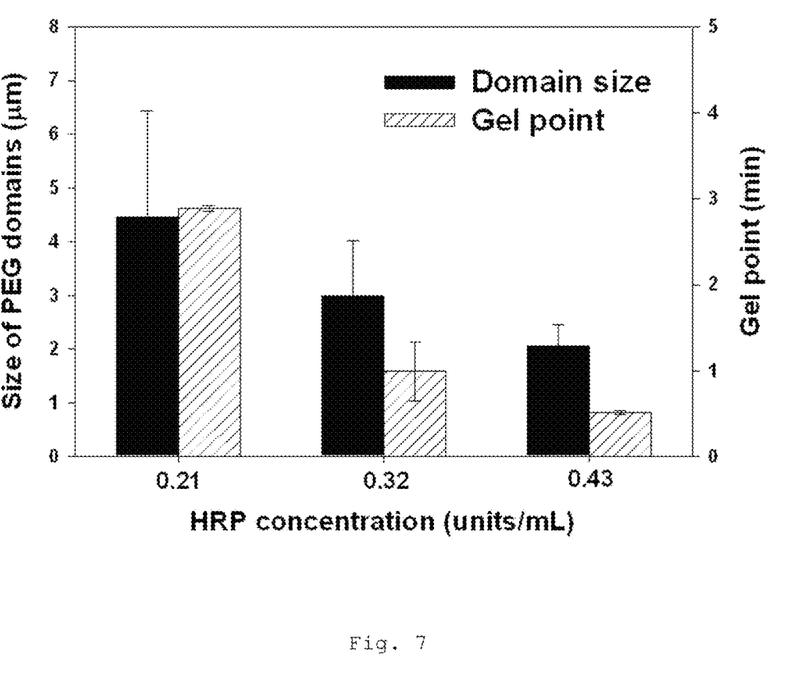
FIG. 7 is a bar graph depicting the diameter of discrete regions in polymeric systems prepared with varying concentrations of catalyst.

As presented in FIG. 7, the diameter of PEG microdomains decreased from 4.5±1.9 to 2.1±0.4 µm when the concentration of HRP increased from 0.21 to 0.43 units/mL. This reduction in the domain sizes can be explained by the inhibition of coalescence of PEG phase droplets in the dextran-tyramine phase during a gelation process. Taken together, these results demonstrated that the size of PEG microdomains could be controlled by simply changing the gelation rate.

Example 4

In Vitro Protein Release from Dextran-Tyramine/PEG Hydrogels with Phase-Separated Structure Dextran-tyramine/PEG hydrogels loaded with PEGASYS were prepared according to the procedure described in Example 3. Typically, 270 µL of dextran-tyramine solution, 30 µL of PEG solution and 6 µL of PEGASYS (360 µg/mL) were mixed in a Protein LoBind microcentrifuge tube. Subsequently, 3 µL of HRP and 3 µL of $H_2O_2$ solution in varying concentrations were added. The mixture was immediately vortexed and 210 µL of the resultant mixture was injected between two parallel glass plates clamped together with 1.5 mm spacing. Gelation was allowed to proceed for 1 hour at 37° C. on an orbital shaker at 50 rpm. For comparison, protein-loaded dextran-tyramine hydrogels were prepared using 30 µL of distilled water instead of PEG solution.

Each hydrogel disk (13 mm diameter×1.5 mm thick) was placed in a vial and then immersed in 20 mL of 10 mM PBS solution (pH 7.4) containing bovine serum albumin and sodium azide at a concentration of 0.05% (w/v). The samples were incubated at 37° C. on an orbital shaker at 50 rpm. At definite time intervals, 200 µL of the release medium was collected and stored at −20° C. To keep the total volume constant, 200 µL of fresh buffer solution was added to the vial. The protein concentrations in the collected samples were measured by using a VeriKine human interferon-alpha ELISA kit. The cumulative percentage of protein release was determined by dividing the amount of released proteins with the amount of proteins added to each hydrogel.

Figure 8:
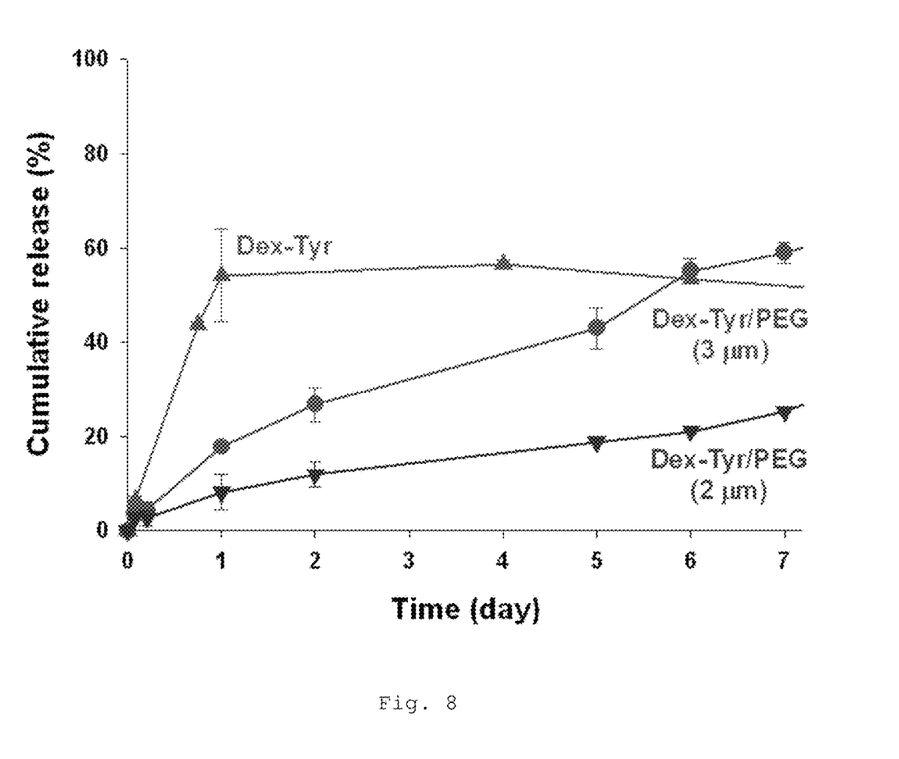
FIG. 8 depicts short-term in vitro release profiles of PEGASYS (Peginterferon alpha-2a) from dextran-tyramine/PEG hydrogels with different PEG domain sizes.
Figure 9:
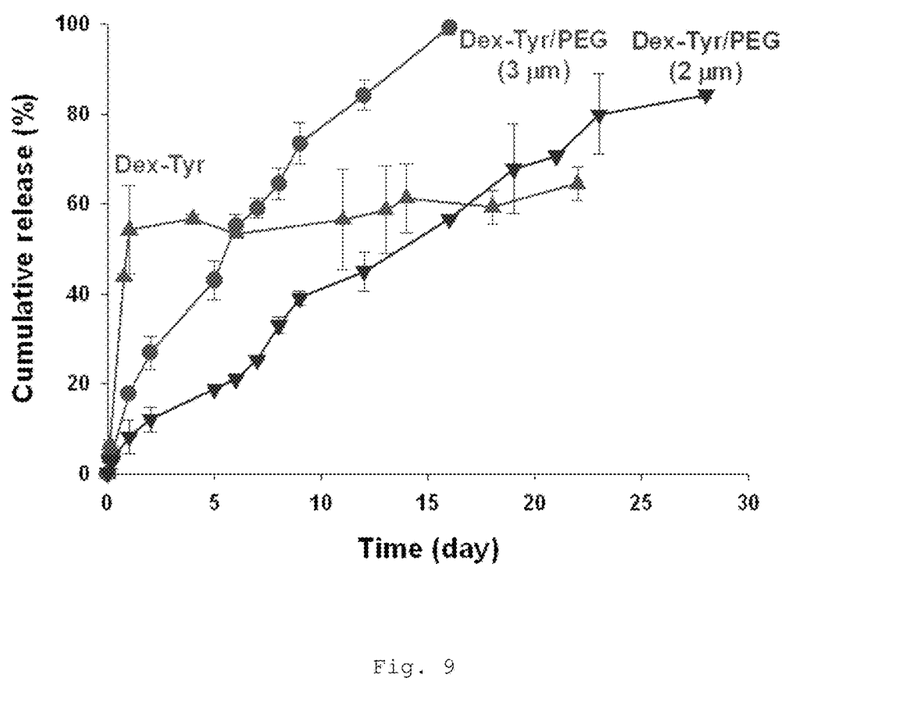
FIG. 9 depicts long-term in vitro release profiles of PEGASYS (Peginterferon alpha-2a) from dextran-tyramine/PEG hydrogels with different PEG domain sizes.

FIGS. 8 and 9 show the release profiles of PEGASYS from dextran-tyramine and dextran-tyramine/PEG hydrogels in PBS (pH 7.4). The dextran-tyramine hydrogels without PEG domains displayed a rapid protein release; around 55% of the encapsulated proteins were released within 1 day. This implies that the proteins encapsulated in the dextran-tyramine hydrogels rapidly diffused out of the gel network due to a high protein concentration gradient. On the contrary, a sustained release of PEGASYS was observed in the case of dextran-tyramine/PEG hydrogels. The dextran-tyramine/PEG hydrogels with 2 µm domains released PEGASYS for 1 month in a sustained manner. This result suggested that the presence of PEG microdomains effectively suppressed the initial burst release of proteins from the hydrogels. It was also noteworthy that dextran-tyramine/PEG hydrogels with 2 µm domains exhibited slower protein release, as compared with those with larger PEG domains (3 µm). While the dextran-tyramine/PEG hydrogels with 2 µm domains released 25.1±0.2% of the encapsulated proteins within 7 days, the hydrogels with 3 µm domains showed a protein release of 58.9±2.1% during the same period. Thus the above results revealed that the release rate of PEGASYS was regulated by changing the size of PEG domains through the control of gelation rate.

It is also to be noted that when the release rate of PEGylated proteins in dextran-tyramine/PEG hydrogels was compared with that in the case of dextran-methacrylate/PEG hydrogels, the dextran-tyramine/PEG hydrogels showed sustained release of the PEGylated proteins, which is absent from the dextran-methacrylate/PEG hydrogels. Such sustained release cannot be achieved by the dextran-methacrylate/PEG hydrogels in which when insulin was used as the active agent, all of the active agent was quickly released from the dextran-methacrylate/PEG hydrogels within 33 hours (data not shown). In addition, the dextran-methacrylate/PEG hydrogels require an agent such as dextranase to induce release of the loaded insulin. Such a release agent is not needed in the disclosed polymeric system.

Furthermore, dextran-methacrylate/PEG hydrogels regulate the protein release rate by adding varying concentrations of dextranase. However, such an approach is not applicable in vivo because dextranase has a tendency to diffuse out of the hydrogel and into the body due to its small molecular weight. As a result, the concentration of dextranase remaining in dextran-methacrylate/PEG hydrogels significantly decreases over time. Hence, dextran-methacrylate/PEG hydrogels cannot effectively control the release of the loaded proteins over an extended period of time when injected into the body.

In contrast, the disclosed polymeric system regulates the release rate of PEGylated proteins by changing the size of PEG microdomains. Since the size of PEG microdomains does not vary over time once formed in the body, the disclosed polymeric system can control the release of the loaded proteins over an extended period of time.

Comparative Example 1

Comparative Study of Using Dextran Over Hyaluronic Acid (HA) in Hydrogels

Dextran-based hydrogels have longer residence time in the body than HA-based hydrogels. HA is degraded by hyaluronidase, while dextran is degraded by dextranase. Since hyaluronidase is more abundantly produced in the body than dextranase, HA-based hydrogels are more quickly degraded in the body than dextran-based hydrogels. Therefore, dextran-based hydrogels are more suitable as long-term protein delivery systems. Additionally, dextran-based hydrogels are more cost-effective because dextran is much cheaper than HA.

Applications

The disclosed polymeric system for release of an active agent is particularly advantageous for sustained and controlled delivery of various active agents. In particular, it has been shown that the release rate of the active agent can be controlled by changing the size of the discrete regions of the first polymeric phase. This can be achieved by controlling the concentration of the catalyst for cross-linking between the phenol moieties (or phenol-containing moieties) during polymerization.

The disclosed polymeric system may be applied to an injectable hydrogel for release of an active agent, as well as a carrier for delivering a biologically active substance or a drug, comprising the injectable hydrogel as an active ingredient. This advantageously prepares injectable hydrogels and carriers that can be applied for sustained and controlled delivery of various active agents.

These hydrogels can be utilized as tissue engineering matrices, wound dressings, dermal fillers, and drug delivery devices. In particular, they may be used as protein drug delivery systems that can form a stable depot in the body in situ and release their payloads in a sustained manner. Advantageously, the use of injectable in situ forming hydrogels may eliminate the need for surgical procedures, which would otherwise have been required to implant pre-formed hydrogels. In situ formed hydrogels carrying bioactive agents can be readily injected into locations that are hard to access through surgery. This feature is also beneficial in reducing the recovery time and the risk of infection in patients. Consequently, this reduces patient discomfort and the cost of treatment.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A polymeric system for release of an active agent, having a first polymeric phase comprising polyethylene glycol (PEG) and containing the active agent as a PEG conjugated-active agent, said first polymeric phase forming discrete regions of a set size range and being dispersed within a second polymeric phase comprising a cross-linked dextran-tyramine conjugate for release of the active agent therein, wherein said PEG conjugated-active agent preferentially partitions to said first polymeric phase as compared to said second polymeric phase and wherein the first polymeric phase comprising PEG is not conjugated to the active agent.

2. The polymeric system of claim 1, wherein the second polymeric phase has been formed by utilizing an agent that controls the rate of cross-linking during formation of said second polymeric phase to thereby control the set size range of the discrete regions of the first polymer phase.

3. The polymeric system of claim 2, wherein the agent that controls the rate of cross-linking during polymerization is a catalyst, and wherein said catalyst is selected from the group consisting of horseradish peroxidase, human myeloperoxidase, lactoperoxidase, eosinophil peroxidase, thyroid peroxidase, prostaglandin H synthases, soybean peroxidase, hemin, hematin, microperoxidase-11, and cytochrome c.

4. The polymeric system of claim 1, wherein the rate of release of said active agent from said polymeric system is dependent on the size of said discrete regions, such that smaller discrete regions result in a slower release rate of said active agent from said polymeric system as compared to larger discrete regions.

5. The polymeric system of claim 1, wherein the size of said discrete regions is in the micron-range or the nano-range and the discrete regions form microdomains, microspheres or microcapsules.

6. The polymeric system of claim 1, wherein said active agent is selected from the group consisting of proteins, antibodies, peptides, small-molecule drugs, nucleic acid-based drugs, nanoparticulate systems and mixtures thereof.

7. The polymeric system of claim 1, wherein said PEG conjugated-active agent is PEGinterferon alpha-2a, PEGylated L-asparaginase, PEG-adenosine deaminase, PEGinesatide, PEGylated uricase, PEGylated hyaluronidase, PEGylated epidermal growth factor, PEGylated tumor necrosis factor, PEGylated tumor necrosis factor-related apoptosis-inducing ligand, certolizumab pegol, PEGylated erythropoetin, PEGaptanib, PEGylated recombinant methionyl human granulocyte colony-stimulating factor, PEG-human growth hormone mutein antagonists and PEGylated interferon alpha-2b.

8. An injectable hydrogel for release of an active agent, having a first polymeric phase comprising polyethylene glycol (PEG) and containing the active agent as a PEG conjugated-active agent, said first polymeric phase forming discrete regions of a set size range and being dispersed within a second polymeric phase comprising a cross-linked dextran-tyramine conjugate for release of the active agent therein, wherein said PEG conjugated-active agent preferentially partitions to said first polymeric phase as compared to said second polymeric phase and wherein the first polymeric phase comprising PEG is not conjugated to the active agent.

9. A method for forming a polymeric system for release of an active agent, having a first polymeric phase comprising polyethylene glycol (PEG) and containing the active agent as a PEG conjugated-active agent, said first polymeric phase forming discrete regions of a set size range and being dispersed within a second polymeric phase comprising a cross-linked dextran-tyramine conjugate for release of the active agent therein, wherein said PEG conjugated-active agent preferentially partitions to said first polymeric phase as compared to said second polymeric phase and wherein the first polymeric phase comprising PEG is not conjugated to the active agent, the method comprising the steps of:
a) providing an aqueous reaction mixture comprising the first polymeric phase polymer, the dextran-tyramine conjugate and the PEG conjugated-active agent; and
b) controlling the rate of cross-linking of said dextran-tyramine conjugate during formation of said second polymeric phase to thereby control the set size range of the discrete regions of the first polymeric phase having the PEG conjugated-active agent therein.

10. The method of claim 9, comprising the step of adding an agent that controls the rate of cross-linking of said second polymeric phase to said reaction mixture.

11. The method of claim 10, comprising the step of selecting the concentration of said agent to thereby control the rate of cross-linking of said second polymeric phase.

12. The method of claim 9, wherein said cross-linking step involves the formation of a C—C bond or C—O bond between a pair of dextran-tyramine conjugates.

13. The method of claim 9, comprising the step of adding an oxidizing agent to said reaction mixture, wherein said oxidizing agent is a peroxide selected from hydrogen peroxide, sodium peroxide, potassium peroxide, hydrogen superoxide, potassium superoxide, alkyl peroxides, aryl peroxides, acyl peroxides, organic hydroperoxides, organic peracids, sodium percarbonate, ammonium persulfate and perborates.

14. The method of claim 9, wherein said crosslinking is carried out for 1 to 60 minutes, or at a temperature of 4° C. to 40° C.

15. The method of claim 10, wherein said agent is a catalyst, wherein said catalyst is an enzyme selected from horseradish peroxidase, human myeloperoxidase, lactoperoxidase, eosinophil peroxidase, thyroid peroxidase, prostaglandin H synthases, soybean peroxidase, hemin, hematin, microperoxidase-11, and cytochrome c.

16. The polymeric system of claim 1, wherein said active agent is selected from the group consisting of insulin, bovine serum albumin and interferon.

* * * * *